(12) United States Patent
Fischer

(10) Patent No.: US 11,179,189 B2
(45) Date of Patent: Nov. 23, 2021

(54) MONOPOLAR ELECTROSURGICAL INSTRUMENT, ELECTROSURGICAL SYSTEM, AND METHOD FOR PRODUCING AN ELECTROSURGICAL INSTRUMENT

(71) Applicant: OLYMPUS WINTER & IBE GMBH, Hamburg (DE)

(72) Inventor: Uwe Fischer, Berlin (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 466 days.

(21) Appl. No.: 16/090,895

(22) PCT Filed: May 4, 2017

(86) PCT No.: PCT/EP2017/060724
§ 371 (c)(1),
(2) Date: Oct. 3, 2018

(87) PCT Pub. No.: WO2017/211509
PCT Pub. Date: Dec. 14, 2017

(65) Prior Publication Data
US 2019/0069944 A1     Mar. 7, 2019

(30) Foreign Application Priority Data

Jun. 10, 2016  (DE) .................. 102016110705.0

(51) Int. Cl.
*A61B 18/12*    (2006.01)
*A61B 18/04*    (2006.01)
*A61B 18/00*    (2006.01)

(52) U.S. Cl.
CPC ........ *A61B 18/1206* (2013.01); *A61B 18/042* (2013.01); *A61B 2018/00077* (2013.01);
(Continued)

(58) Field of Classification Search
CPC .............. A61B 18/1206; A61B 18/042; A61B 2018/00077; A61B 2018/00148;
(Continued)

(56) References Cited

U.S. PATENT DOCUMENTS

| | | | |
|---|---|---|---|
| 6,197,026 B1* | 3/2001 | Farin | A61B 18/042 219/121.5 |
| 2004/0115477 A1* | 6/2004 | Nesbitt | A47J 36/025 428/692.1 |

(Continued)

FOREIGN PATENT DOCUMENTS

| | | |
|---|---|---|
| EP | 0765638 A1 * | 4/1997 ........... A61B 18/042 |
| EP | 0765638 A1 | 4/1997 |

(Continued)

OTHER PUBLICATIONS

Jul. 11, 2017 International Search Report issued in International Patent Application No. PCT/EP2017/060724.

(Continued)

*Primary Examiner* — Linda C Dvorak
*Assistant Examiner* — Nils A Potter
(74) *Attorney, Agent, or Firm* — Oliff PLC

(57) ABSTRACT

A monopolar electrosurgical instrument and electrosurgical system for treating biological tissue by a plasma. The instrument includes a tubular line for conducting a gas to the treatment location, wherein the line consists of electrically insulating material and has a distal opening for the exit of the gas in the direction of the tissue to be treated, and an electrode arranged in the region of the distal opening in the line, wherein the electrode is connectable to an electrosurgical generator to ignite a plasma discharge in the gas. Improving the ignition behavior, the inner surface of the line has an enhanced electrical conductivity in the distal opening. Furthermore, a method for producing an electrosurgical (Continued)

instrument for providing a line made of nonconductive material, an electrode, and enhancing the conductivity of an inner surface of the line in the region of the opening, for enhancing the conductivity in the line.

17 Claims, 4 Drawing Sheets

(52) U.S. Cl.
  CPC ............... *A61B 2018/00148* (2013.01); *A61B 2018/00583* (2013.01); *A61B 2018/122* (2013.01); *A61B 2018/1253* (2013.01)

(58) Field of Classification Search
  CPC .... A61B 2018/00583; A61B 2018/122; A61B 2018/1253; A61N 1/44; A61N 7/00; H05B 7/00
  USPC .......................................................... 606/41
  See application file for complete search history.

(56) References Cited

U.S. PATENT DOCUMENTS

| | | | |
|---|---|---|---|
| 2005/0251134 A1* | 11/2005 | Woloszko | A61B 18/149 606/46 |
| 2013/0090643 A1* | 4/2013 | Williams | A61B 18/042 606/40 |
| 2014/0225495 A1* | 8/2014 | Koo | H05H 1/28 313/13 |
| 2015/0038790 A1 | 2/2015 | Rontal et al. | |
| 2015/0305795 A1* | 10/2015 | Varney | A61B 18/042 606/29 |
| 2016/0192980 A1* | 7/2016 | Newton | A61B 18/1445 606/34 |
| 2017/0189109 A1 | 7/2017 | Varney | |
| 2018/0368879 A1* | 12/2018 | Akagane | A61B 18/12 |

FOREIGN PATENT DOCUMENTS

| | | |
|---|---|---|
| EP | 0956827 A1 | 11/1999 |
| JP | H05-049179 U | 6/1993 |
| JP | H09-164149 A | 6/1997 |

OTHER PUBLICATIONS

Jul. 11, 2017 Written Opinion issued in International Patent Application No. PCT/EP2017/060724.

Feb. 2, 2021 Office Action issued in Japanese Patent Application No. 2018-564411.

\* cited by examiner

MONOPOLAR ELECTROSURGICAL INSTRUMENT, ELECTROSURGICAL SYSTEM, AND METHOD FOR PRODUCING AN ELECTROSURGICAL INSTRUMENT

BACKGROUND

The invention relates to a monopolar electrosurgical instrument for treating biological tissue by means of a plasma, having a tubular line for conducting a gas to the treatment location, wherein the line consists of electrically insulating material and has a distal opening for the exit of the gas in the direction of the tissue to be treated, and having an electrode arranged in the region of the distal opening in the line, wherein the electrode is connectable to an electrosurgical generator to ignite a discharge in the gas.

The invention furthermore relates to an electrosurgical system, having an electrosurgical generator, a gas source, and an electrosurgical instrument.

The invention also relates to a method for producing an electrosurgical instrument.

Such instruments and systems have been known for some time. They are used in surgery, for example, to ablate and/or coagulate larger superficial tissue regions, to thus, for example, staunch diffuse bleeding. Argon is usually used as the gas here, this form of treatment is therefore also referred to as argon plasma coagulation (APC). Electrosurgical instruments for APC are also referred to as APC probes.

The main areas of application for APC are gastroenterology and increasingly also laparoscopic surgery. While only very thin APC probes are usable in gastroenterology, larger diameters can also be used in laparoscopic surgery. A larger diameter of the line enables a higher gas flow and thus a better treatment effect.

In APC, a gas flow is firstly initiated through the line, subsequently a high-frequency voltage is applied to the electrode in order to ignite a discharge in the gas. In the case of monopolar APC probes, the voltage is applied between the electrode and a large-area neutral electrode arranged remotely from the treatment site, and therefore the discharge is ignited between the electrode and the tissue to be treated. In the case of bipolar APC probes, a second electrode is arranged in the instrument and the discharge is ignited between the two electrodes.

In particular in the case of monopolar APC probes, it has been shown that very high voltages are required to ignite the discharge in particular in the case of instruments having large diameter. In spite of providing a correspondingly high voltage, an unacceptably long time is often required between the application of the voltage and the ignition of the discharge, it can even occur that an ignition cannot be achieved.

SUMMARY

The object of the invention is therefore to provide a monopolar electrosurgical instrument and an electrosurgical system, which are improved with respect to the described disadvantages.

This object is achieved according to the invention by a monopolar electrosurgical instrument for treating biological tissue by means of a plasma, having a tubular line for conducting a gas to the treatment location, wherein the line consists of electrically insulating material and has a distal opening for the exit of the gas in the direction of the tissue to be treated, and having an electrode arranged in the region of the distal opening in the line, wherein the electrode is connectable to an electrosurgical generator to ignite a discharge in the gas, which is refined in that the inner surface of the line has an enhanced electrical conductivity in the region of the distal opening.

The section of the inner surface of the line in which the electrical conductivity is enhanced is not connected to one of the poles of the electrosurgical generator during the usage of the instrument.

Experiments of the inventor have shown that the ignition procedure of a corresponding instrument takes place in two steps. Firstly a corona discharge is ignited in the region of the electrode, which is superseded after a short time by an electric arc discharge, which generates the therapeutically usable plasma.

It has been shown that the ignition of the corona discharge takes place significantly more easily due to the provision of an enhanced electrical conductivity of the inner surface of the line in the region of the distal opening, and therefore the electric arc discharge can subsequently be ignited reliably. This is attributed to the fact that high field gradients, which promote the discharge, occur at an interface between the conductive surface and the nonconductive material, which generally has a high dielectric constant.

In one possible embodiment of the invention, a sleeve-shaped insert, the inner surface of which has the enhanced electrical conductivity, is arranged in the line in the region of the opening.

This insert can be a metal sleeve. However, an undesired current path can arise in the APC probe in this way, in the case of which a flashover occurs from the probe to the metal sleeve and then from the metal sleeve to the tissue to be treated. The insert therefore preferably also consists of nonconductive material.

In a further possible embodiment of the invention, the inner surface of the line or the insert has a conductivity enhanced by thermal or electrochemical treatment in the region of the distal opening. Thus, for example, the surface of a line or an insert made of hydrocarbon or fluorocarbon materials (for example, polyethylene (PE), polypropylene (PP), polytetrafluoroethylene (PTFE)) can be carbonized by heating or by electrical discharges, at the same time the polymers on the surface are broken up and a conductive carbon layer forms.

In an alternative embodiment of the invention, the inner surface of the line or the insert is coated using a conductive substance in the region of the distal opening. This can be carried out, for example, by applying a conductive lacquer, vapor deposition using a metal, or by rubbing on a soft graphite rod. It has been shown that the coating does not have to be durable. Rather, it is sufficient if the coating is provided at the point in time of the first ignition of the APC probe. This is because it has surprisingly been shown that subsequent ignition procedures are possible rapidly and reliably after ignition has taken place once independently of a durable coating.

In a further alternative embodiment of the invention, a conductive substance is embedded in the material of the line or the insert in the region of the distal opening. The conductive substance is preferably embedded in the form of fibers or filaments in the material of the line or the insert.

The conductive substance of the above-described embodiments can be carbon or the conductive substance can contain carbon. Carbon is physiologically harmless and has a good conductivity.

Alternatively, the conductive substance can be or contain a metal. Some metals are also physiologically harmless and also have a good conductivity, for example, gold, iron, titanium.

The object is furthermore achieved by an electrosurgical system having an electrosurgical generator, a gas source, and an electrosurgical instrument according to the above embodiments. APC treatments may be carried out reliably and safely using such an electrosurgical system.

The object is also achieved by a method for producing an electrosurgical instrument according to the above embodiments having the following steps:
providing a line made of nonconductive material,
providing an electrode,
positioning the electrode in the line in the region of a distal opening of the line,
enhancing the conductivity of an inner surface of the line in the region of the opening, wherein the step of enhancing the conductivity can take place before or after the step of positioning the electrode in the line, and wherein the electrode is not connected to a voltage source during the step of enhancing the conductivity.

The corresponding method may be automated particularly easily, since a complex temporary connection of the electrode to a voltage source is omitted.

BRIEF DESCRIPTION OF THE DRAWINGS

The invention will be explained in greater detail hereafter on the basis of several exemplary figures. In the figures

DETAILED DESCRIPTION OF EMBODIMENTS

Figure 1:
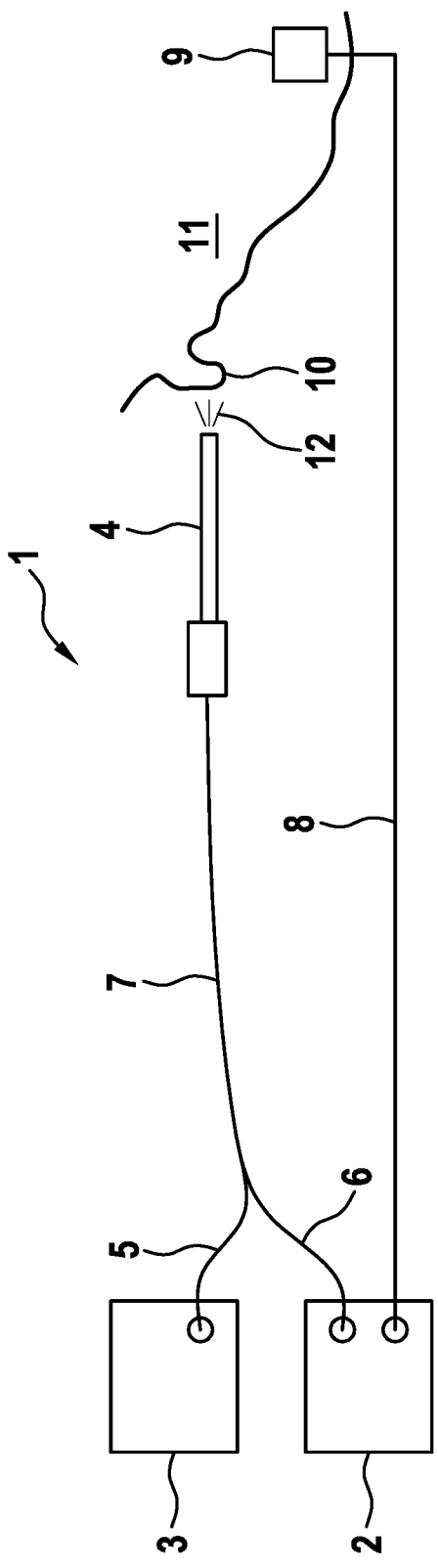
FIG. 1: shows an electrosurgical system in a schematic illustration.

FIG. 1 shows an electrosurgical system 1 having an electrosurgical generator 2, a gas source 3, and an electrosurgical instrument in the form of an APC probe 4. The electrosurgical generator 2 can be, for example, a generator of the type ESG-300 of the applicant. Such generators are well-known, because of which a more detailed description will be omitted here. The gas source 3 is configured to dispense gas in a controlled manner from a suitable reservoir, for example, a gas bottle or a central gas supply of a medical device can be used as the reservoir. The gas is preferably a noble gas, for example, argon. The gas source can be, for example, a device of the type APU-300 of the applicant.

The gas source 3 is connected via a gas line 5 to the APC probe 4. An output of the electrosurgical generator 2 is connected via a line 6 to the APC probe 4. Gas line 5 and line 6 can be combined over a large part of the length thereof to form a supply line 7, in order to facilitate the handling of the APC probe 4.

A second output of the electrosurgical generator 2 is connected via a line 8 to a neutral electrode 9.

To treat a section 10 of a tissue mass 11, the neutral electrode 9 is connected to the tissue 11 as far away as possible from the section 10. In the case of laparoscopic or gastroenterological procedures, the neutral electrode 9 is fastened for this purpose on a thigh of the patient. The APC probe 4 is positioned in the vicinity of the section 10.

The electrosurgical generator 2 and the gas source 3 are then activated, and therefore a flow 12 of ionized gas is dispensed in the direction of the section 10 of the tissue 11 and staunches a superficial bleeding there, for example. The power circuit required for generating the ionized gas extends from the electrosurgical generator 2 via the line 6 to the APC probe 4, from there through the gas flow 12 into the tissue 11, and then via the neutral electrode 9 and the line 8 back to the electrosurgical generator 2. Since it is an alternating current, the current also flows in the opposite direction, of course.

The neutral electrode 9 is embodied having a large surface area, and therefore as the current passes over between tissue 11 and neutral electrode 9, only low current densities occur and the tissue 11 outside the section 10 to be treated is not damaged.

In a bipolar embodiment (not shown) of an electrosurgical system, the neutral electrode 9 is omitted, instead the power circuit is closed via two electrodes provided in the APC probe.

Figure 2:
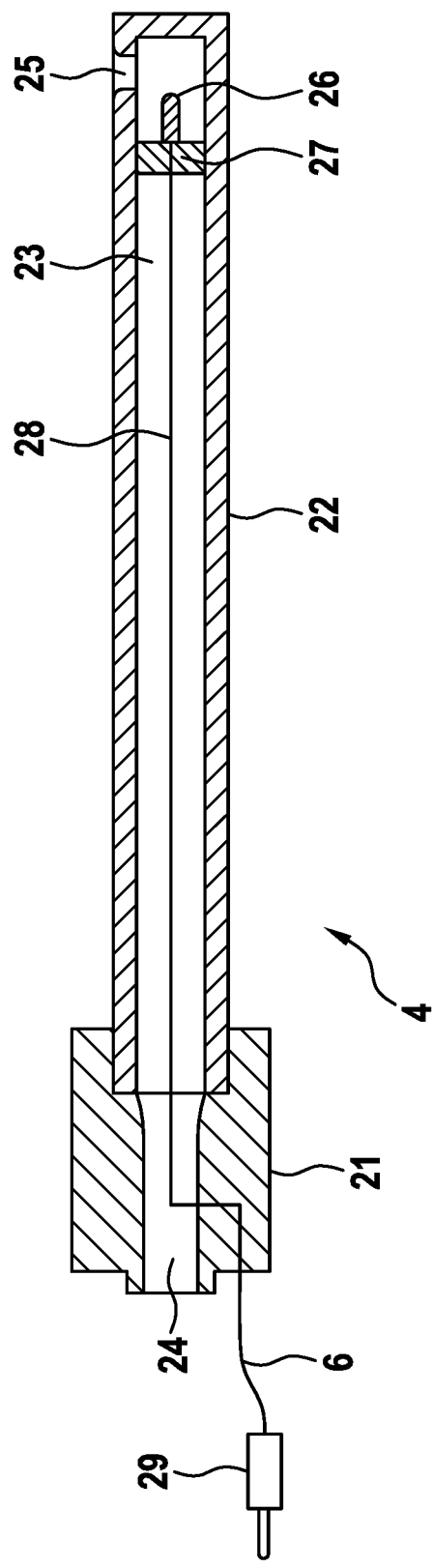
FIG. 2: shows an electrosurgical instrument according to the prior art.

The APC probe 4 is shown in longitudinal section in FIG. 2. The APC probe 4 comprises a main body 21 and a tubular line 22. Depending on the field of use, the line 22 can be a rigid hollow shaft or a flexible hose. A rigid hollow shaft will primarily be used in open and laparoscopic surgery, while a flexible hose is primarily used in gastroenterology.

The line 22 is fastened with its proximal end in the main body 21, for example, by means of an adhesive bond, wherein an inner lumen 23 of the line 22 opens into an inner lumen 24 of the main body 21.

A distal opening 25, through which gas can be dispensed in the direction of the tissue to be treated, is provided at the distal end of the line 22. In the illustrated example, the distal opening 25 is oriented perpendicularly to the longitudinal extension of the APC probe 4. Alternatively, the distal opening 25 can also be oriented in deviating directions.

An electrode 26 is positioned and fastened by means of a retaining element 27 close to the distal opening 25 in the line 22. The retaining element is designed in this case such that it is supported on multiple points on the line 22, without significantly constricting the inner lumen 23. An electrical feed line 28 is connected distally to the electrode 26 and extends in the proximal direction of the line 22. The feed line 28 is led out of the lumen 24 at the main body 21. Outside the main body 21, the feed line merges into the line 6 and can be connected via a plug 29 to the electrosurgical generator 2.

A gas line 5 (not shown in FIG. 2) can be fastened at the proximal end of the lumen 24 in order to supply the APC probe 4 with gas.

Various exemplary embodiments of the distal end of an APC probe are shown in FIGS. 3 to 6.

Figure 3:
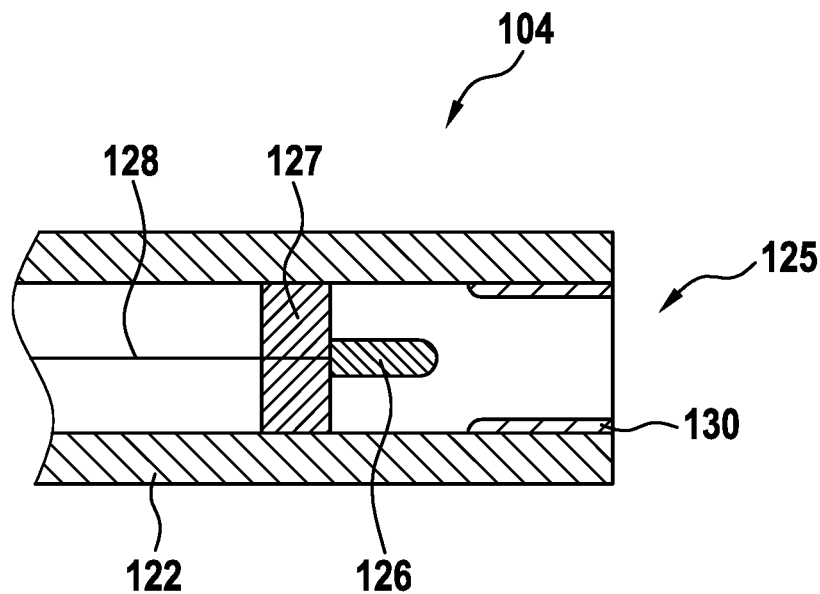
FIG. 3: shows an embodiment of an electrosurgical instrument.

FIG. 3 shows the distal end of a monopolar APC probe 104, the distal opening 125 of which is oriented in the direction of the longitudinal axis of the APC probe 104. The APC probe 104 again comprises a tubular line 122, in which an electrode 126 is fastened by means of a retaining element 127. An electrical feed line 128 for connecting the electrode 126 to an electrosurgical generator is also shown.

The inner surface of the line 122 is provided with a conductive coating 130 in the region of the distal opening 125. In this case, this can be an electrically conductive lacquer, also called conductive lacquer. This conductive lacquer preferably consists of a binding matrix, for example, artificial resin, and a conductive powdered filler material such as silver, copper, or graphite.

The conductive coating 130 can alternatively also be a binder-free coating, for example, a graphite layer. A limited mechanical stability of the coating can be accepted, since it is only necessary during the first ignition procedure of the APC probe.

The conductive coating 130 is not in electrical contact with one of the poles of the electrosurgical generator (2 in FIG. 1). This applies similarly to all following exemplary embodiments.

Figure 4:
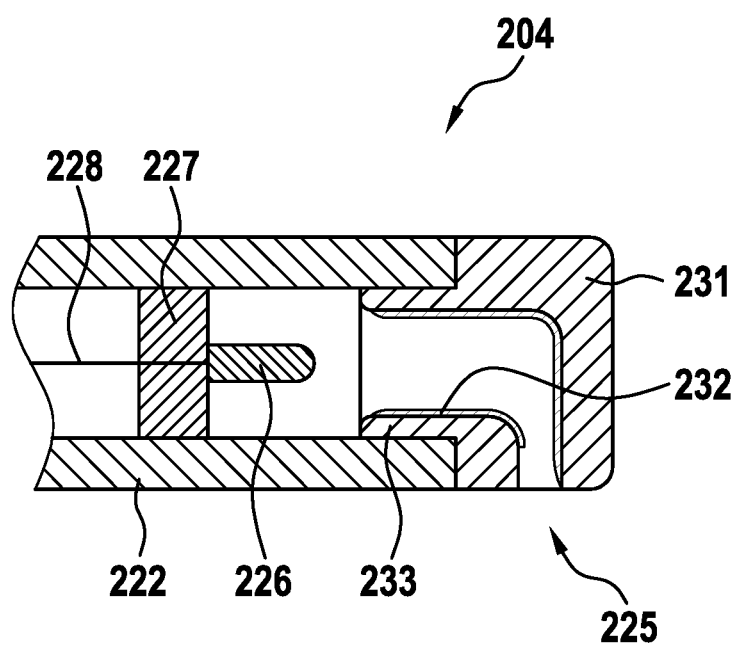
FIG. 4: shows a second embodiment of an electrosurgical instrument.

FIG. 4 shows the distal end of a further APC probe 204. The APC probe 204 again has a tubular line 222, an electrode 226, a retaining element 227, and an electrical feed line 228. A sleeve-shaped insert 231, the inner surface 232 of which has an enhanced electrical conductivity, is inserted into the distal end of the line 222. The insert 231 preferably consists of a plastic or a ceramic, the inner surface 232 is enhanced in its conductivity by etching or annealing, for example.

A lateral distal opening 225 is provided in the insert 231. The plasma flow is dispensed in operation of the APC probe 204 transversely to its longitudinal axis through the opening 225.

To fasten the insert 231 in the line 222, it has a collar 233, which is pushed into the line 222 and is fixed therein by a press fit. To enhance the stability, the insert 231 can additionally be adhesively bonded to the line 222.

Figure 5:
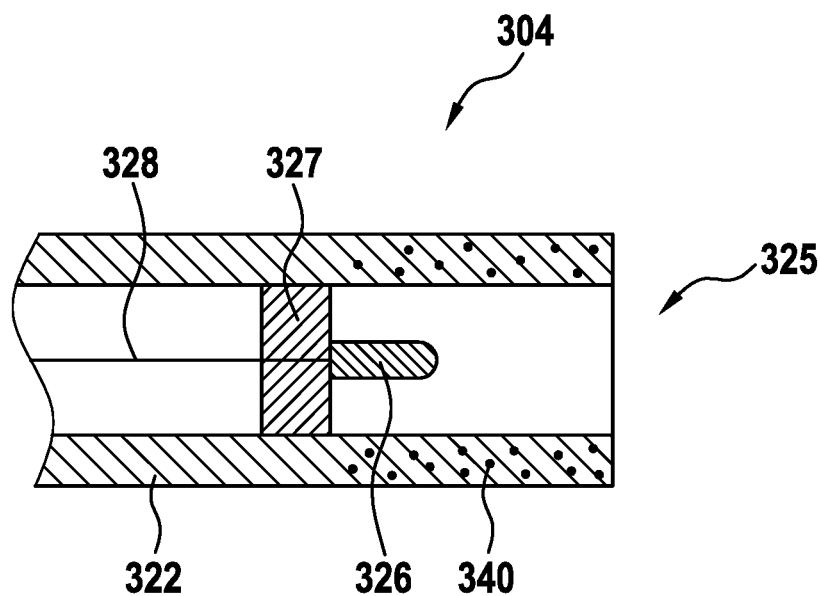
FIG. 5: shows a third embodiment of an electrosurgical instrument.

FIG. 5 shows a further APC probe 304, this again has a tubular line 322, an electrode 326 having retaining element 327, and an electrical feed line 328. The line 322 forms a distal opening 325 aligned in the direction of its longitudinal axis at the distal end.

Conductive particles 340 are embedded in the material of the line 322 in the region of the distal opening 325. In this case, these can be graphite bodies, carbon fibers, or metal chips, for example. The particles are embedded in a low density in the material of the line 322, and therefore they are not connected to one another and only the particles exposed in the region of the inner surface of the line 322 contribute to a locally enhanced conductivity.

To produce the line 322, for example, particles 340 can be added to the strand material at defined intervals in an endless production process such as strand extruding. The endless strand is subsequently cut in the region of the added particles 340, and therefore individual line sections result, in the ends of which particles 340 are embedded.

Figure 6:
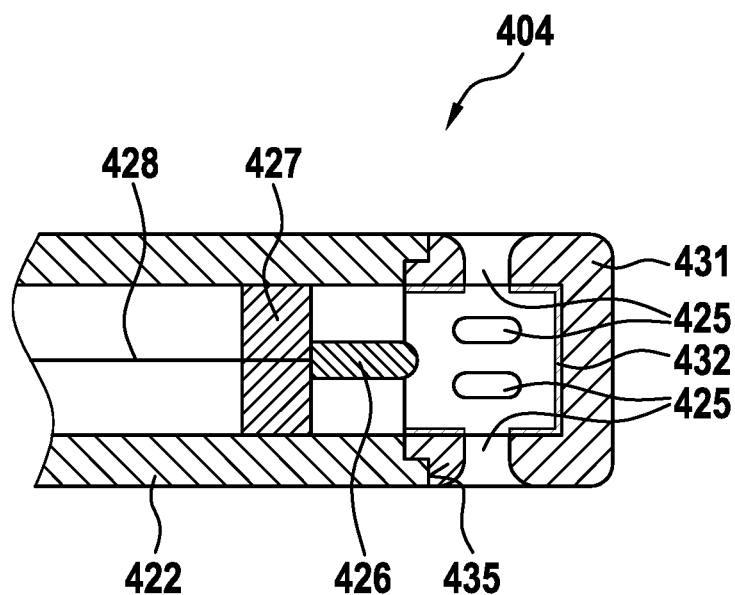
FIG. 6: shows a fourth embodiment of an electrosurgical instrument.

FIG. 6 shows a further APC probe 404, which also comprises a tubular line 422, an electrode 426 having retaining element 427, and electrical feed line 428. Similarly as shown in FIG. 4, the line 422 is terminated by a sleeve-shaped insert 431, the inner surface of which is treated to enhance the conductivity. Reference is made to the description of FIG. 4 with respect to the surface treatment.

In contrast to the illustration in FIG. 4, the insert 431 has multiple distal openings 425 arranged along its circumference, and therefore the APC probe 404 dispenses a radial plasma flow in operation. This can be used, for example, to treat the complete inner surface of a tubular hollow organ.

To fasten the insert 431 on the line 422, both have a stepped end face 435. The end faces 435 are adhesively bonded to one another, for example.

The embodiments shown in FIGS. 3 to 6 can be combined with one another without exercising inventive skill. Thus, for example, a coating according to FIG. 3 or an embedding of conductive particles according to FIG. 5 can also take place upon use of a sleeve-type insert according to FIGS. 4 and/or 6. Alternatively, the inner surface of the tubular line in embodiments according to FIGS. 3 and/or 4 can be enhanced directly in its conductivity by electrochemical or thermal treatment, as shown for the sleeve-type inserts according to FIGS. 4 and/or 6.

Figure 7:
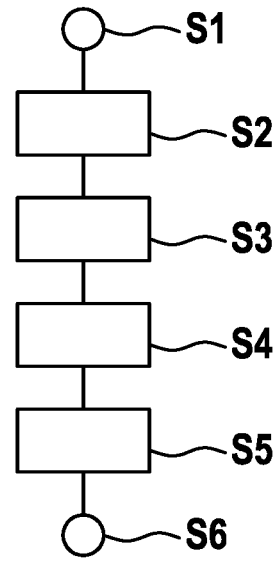
FIG. 7: shows a flow chart of a first method for producing an electrosurgical instrument.

FIG. 7 schematically shows a method for producing a surgical instrument. For this purpose, after the beginning of the method in step S1, a line made of nonconductive material is provided in a step S2. In a next step S3, an electrode is then provided. In a step S4, the electrode is then positioned in the region of a distal opening of the line, for example, while using a retaining element.

In a step S5, the conductivity of an inner surface of the line is enhanced. During step S5, the electrode is not connected to a voltage source, whereby complex contacting measures are omitted. This is preferable in particular in the context of an automated production.

After step S5, the end of the method is reached in step S6.

In a variant of the method (not shown), step S5 can be placed before step S4. For example, step S5 can be integrated into step S2 to produce a surgical instrument according to FIG. 5, and therefore the line is thus already provided with an enhanced conductivity in the region of its inner surface during its provision.

Figure 8:
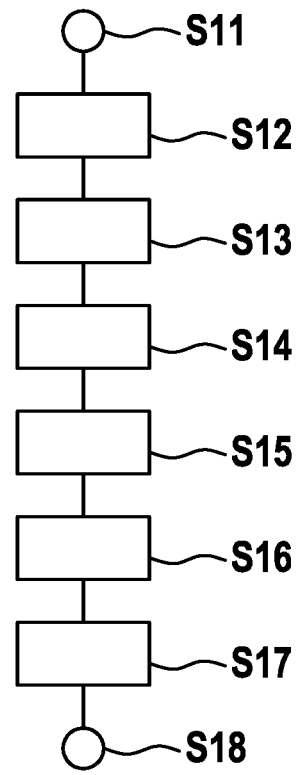
FIG. 8: shows a flow chart of a second method for producing an electrosurgical instrument.

FIG. 8 shows a further possible method for producing a surgical instrument, preferably according to FIG. 4 or 6.

The method is started in a step S11. In a step S12, a tubular line is then provided. Subsequently, an electrode is provided in a step S13 and is positioned in the region of the distal end of the line in a step S14.

Subsequently, a sleeve-type insert is provided in a step S15. The inner surface of the insert is then treated in a step S16 to enhance the conductivity. Finally, in a step S17, the insert is connected to the line, the end of the method is reached thereafter in step S18.

The invention claimed is:

1. A monopolar electrosurgical instrument for treating biological tissue by means of a plasma, the monopolar electrosurgical instrument comprising:
    a tubular line for conducting a gas to the treatment location, wherein the line comprises an electrically insulating material and has a distal opening for the exit of the gas in the direction of the tissue to be treated, and
    an electrode arranged in the region of the distal opening in the line, wherein the electrode is connectable to an electrosurgical generator to ignite a plasma discharge in the gas,
    wherein the inner surface of the line has an enhanced electrical conductivity in the region of the distal opening at a position that is electrically separated from the electrode.

2. The electrosurgical instrument as claimed in claim 1, wherein a sleeve-shaped insert, the inner surface of which has the enhanced electrical conductivity, is arranged in the line in the region of the opening.

3. The electrosurgical instrument as claimed in claim 2, wherein the inner surface of the insert is coated using a conductive substance in the region of the distal opening.

4. The electrosurgical instrument as claimed in claim 2, wherein a conductive substance is embedded in the material of the insert in the region of the distal opening.

5. The electrosurgical instrument as claimed in claim 4, wherein the conductive substance is embedded in the form of fibers or filaments in the material of the insert.

6. The electrosurgical instrument as claimed in claim 1, wherein the inner surface of the line has a conductivity enhanced by thermal or electrochemical treatment in the region of the distal opening.

7. The electrosurgical instrument as claimed in claim 1, wherein the inner surface of the line is coated using a conductive substance in the region of the distal opening.

8. The electrosurgical instrument as claimed in claim 7, wherein the conductive substance is or contains carbon.

9. The electrosurgical instrument as claimed in claim 7, wherein the conductive substance is or contains a metal.

10. The electrosurgical instrument as claimed in claim 1, wherein a conductive substance is embedded in the material of the line in the region of the distal opening.

11. The electrosurgical instrument as claimed in claim 10, wherein the conductive substance is embedded in the form of fibers or filaments in the material of the line.

12. An electrosurgical system, having an electrosurgical generator, a gas source, and an electrosurgical instrument as claimed in claim 1.

13. The electrosurgical system as claimed in claim 12, wherein the region of the inner surface of the line having enhanced conductivity is not attached to the poles of the electrosurgical generator during use of the instrument.

14. A method for producing an electrosurgical instrument as claimed in claim 1 having the following steps:
 providing a line made of nonconductive material,
 providing an electrode,
 positioning the electrode in the line in the region of a distal opening of the line,
 enhancing the conductivity of an inner surface of the line in the region of the opening,
 wherein the step of enhancing the conductivity can take place before or after the step of positioning the electrode in the line, and wherein the electrode is not connected to a voltage source during the step of enhancing the conductivity.

15. A monopolar electrosurgical instrument for treating biological tissue via plasma at a treatment location, the monopolar electrosurgical instrument comprising:
 a tubular line configured to conduct a gas to the treatment location, the tubular line including a distal opening configured to provide an exit for the gas in a direction of the treatment location; and
 an electrode arranged within the tubular line in a region proximal to the distal opening, and configured to connect to an electrosurgical generator and ignite a plasma discharge in a gas,
 wherein an inner surface of the tubular line has an enhanced electrical conductivity in a region between the electrode and the distal opening at a position that is electrically separated from the electrode.

16. An electrosurgical system, having an electrosurgical generator, a gas source, and an electrosurgical instrument as claimed in claim 15.

17. The electrosurgical system as claimed in claim 16, wherein the region of the inner surface of the line having enhanced conductivity is not attached to the poles of the electrosurgical generator during use of the instrument.

* * * * *